United States Patent
Harriman (10) Patent No.: US 8,415,173 B2
(45) Date of Patent: Apr. 9, 2013

(54) GEL MICRODROP COMPOSITION AND METHOD OF USING THE SAME

(75) Inventor: William Don Harriman, Alameda, CA (US)

(73) Assignee: Crystal Bioscience Inc., Emeryville, CA (US)

(*) Notice: Subject to any disclaimer, the term of this patent is extended or adjusted under 35 U.S.C. 154(b) by 0 days.

(21) Appl. No.: 13/219,470

(22) Filed: Aug. 26, 2011

(65) Prior Publication Data
US 2012/0058903 A1 Mar. 8, 2012

Related U.S. Application Data (62) Division of application No. 12/396,278, filed on Mar. 2, 2009, now Pat. No. 8,030,095.

(60) Provisional application No. 61/033,461, filed on Mar. 4, 2008.

(51) Int. Cl.
*G01N 33/544* (2006.01)

(52) U.S. Cl.
USPC ........... 436/535; 436/523; 436/528; 436/529; 436/532; 436/533; 436/546; 436/56; 436/172; 435/6; 435/7.1; 435/7.2; 435/182; 435/287.2; 435/397; 435/403

(58) Field of Classification Search ............. 435/6, 7.1, 435/7.2, 7.5, 397, 403, 287.2; 436/523, 528, 436/529, 532, 533, 535, 546, 56, 166, 172; 422/73, 82.08, 500
See application file for complete search history.

(56) References Cited

U.S. PATENT DOCUMENTS

| 5,627,052 A | 5/1997 | Schrader |
|---|---|---|
| 5,820,879 A | 10/1998 | Fernandez et al. |
| 6,586,176 B1 | 7/2003 | Trnovsky et al. |
| 6,806,058 B2 * | 10/2004 | Jesperson et al. ............. 435/7.5 |
| 6,969,597 B2 | 11/2005 | Lukyanov et al. |
| 7,160,735 B2 | 1/2007 | Dehlinger et al. |
| 7,556,928 B2 | 7/2009 | Jespersen et al. |
| 2004/0005582 A1 | 1/2004 | Shipwash |

(Continued)

FOREIGN PATENT DOCUMENTS

| FR | 2485739 | 12/1981 |
|---|---|---|
| WO | 03/062419 A1 | 7/2003 |

OTHER PUBLICATIONS

PCT Application No. PCT/US09/01357, International Search Report, Jan. 13, 2010.

(Continued)

*Primary Examiner* — Gail R Gabel
(74) *Attorney, Agent, or Firm* — James S. Keddie; Bozicevic, Field & Francis LLP (57) ABSTRACT

A gel microdrop composition is provided. In certain embodiments, the gel microdrop composition contains a polymer matrix, an effector particle that releases an effector molecule into the polymer matrix, a first reporter particle that emits a first optically detectable signal and a second reporter particle that emits a second optically detectable signal that is distinguishable from the first optically detectable signal, where the effector particle and said first and second reporter particles are encapsulated by the polymer matrix. Methods of screening that employ the gel microdrop composition and methods of making the gel microdrop composition are also disclosed.

9 Claims, 3 Drawing Sheets

U.S. PATENT DOCUMENTS

2005/0064498 A1     3/2005   Short et al.
2005/0164162 A1*   7/2005   Sorensen et al. ................ 435/4
2006/0094033 A1     5/2006   Abulencia et al.

OTHER PUBLICATIONS

Atochina, et al., "Comparison of results using the gel microdrop cytokine secretion assay with ELISPOT and intracellular cytokine staining assay", Cytokine, 2004, 27:120-8.

Demirci, et al., "Single cell epitaxy by acoustic picolitre droplets", Lab Chip, 2007, 7:1139-45.

Edd, et al., "Controlled encapsulation of single-cells into monodisperse picolitre drops", Lab Chip, 2008, 8:1262-4.

Friedman, "Inhibition of Antibody Plaque Formation by Sensitized Lymphoid Cells: Rapid Indicator of Transplantation Immunity", Science, 1964, 145:607-9.

Gray, et al., "Secretion capture and report web: use of affinity derivatized agarose microdroplets for the selection of hybridoma cells", J Immunol Methods, 1995, 182:155-63.

Huston, et al., "Protein engineering of antibody binding sites: recovery of specific activity in an anti-digoxin single-chain Fv analogue produced in *Escherichia coli*", Proc Natl Acad Sci, 1988, 85:5879-83, Aug. 1988.

Kanagawa, "Antibody-mediated activation of T cell clones as a method for screening hybridomas producing antibodies to the T cell receptor", J Immunol Methods, 1988, 110:169-78.

Kenney, et al., "Production of monoclonal antibodies using a secretion capture report web", Biotechnology, 1995, 13:787-90.

Ling, et al., "A cell-laden microfluidic hydrogel", Lab Chip, 2007, 7:756-62.

McGuigan, et al., "Cell encapsulation in sub-mm sized gel modules using replica molding", PLoS One, 2008, 3:e2258.

Powell, et al. "Gel microdroplets and flow cytometry: rapid determination of antibody secretion by individual cells within a cell population", Biotechnology, 1990, 8:333-7.

Riechmann, et al., "Reshaping human antibodies for therapy", Nature, 1988, 332:323-7, March 1984.

Sakai, et al., "Production of cell-enclosing hollow-core agarose microcapsules via jetting in water-immiscible liquid paraffin and formation of embryoid body-like spherical tissues from mouse ES cells enclosed within these microcapsules", Biotechnol Bioeng, 2008, 99:235-43.

Turcanu, et al., "Cell identification and isolation on the basis of cytokine secretion: a novel tool for investigating immune responses", Nat Med, 2001, 7:373-6.

Uludag, et al., "Technology of mammalian cell encapsulation", Adv Drug Deilv Rev, 2000, 42:29-64.

EP App. No. 09717934.5, extended European Search Report, dated Mar. 23, 2012, 6pgs.

* cited by examiner

GEL MICRODROP COMPOSITION AND METHOD OF USING THE SAME

CROSS-REFERENCING

This patent application is a divisional application of U.S. non-provisional application Ser. No. 12/396,278, filed Mar. 2, 2009, now U.S. Pat. No. 8,030,295, which claims the benefit of U.S. provisional application Ser. No. 61/033,461, filed on Mar. 4, 2008, which application is incorporated by reference herein in its entirety.

BACKGROUND

Certain aspects of this disclosure relate to gel microdrops and their use in a screening method to identify biologically active compounds.

SUMMARY

A gel microdrop composition is provided. In certain embodiments, the gel microdrop composition contains a polymer matrix, an effector particle that releases an effector molecule into the polymer matrix, a first reporter particle that emits a first optically detectable signal and a second reporter particle that emits a second optically detectable signal that is distinguishable from the first optically detectable signal, where the effector particle and said first and second reporter particles are encapsulated by the polymer matrix. Methods of screening that employ the gel microdrop composition and methods of making the gel microdrop composition are also disclosed.

DEFINITIONS

The terms "determining", "measuring", "evaluating", "assessing" and "assaying" are used interchangeably herein to refer to any form of measurement, and include determining if an element is present or not. These terms include both quantitative and/or qualitative determinations. Assessing may be relative or absolute. "Determining the presence of" includes determining the amount of something present, as well as determining whether it is present or absent.

The term "contacting" means to bring or put together. As such, a first item is contacted with a second item when the two items are brought or put together, e.g., by touching them to each other or combining them in the same solution.

The phrase "optically-detectable signal" refers to light signal that can be detected by a photodetector, e.g., a light microscope, a spectrophotometer, a fluorescent microscope, a fluorescent sample reader, or a fluorescence activated cell sorter, 3D tomographer, a camera, etc.

The term "fluorescent protein" refers to a protein whose expression can be detected by the presence of fluorescent signal produced by the protein. An fluorescent signal is produced by a protein, for example, when the protein is capable of being excited by a particular wavelength of light and emits another wavelength of light which is detectable.

The terms "polypeptide" and "protein", used interchangeably herein, refer to a polymeric form of amino acids of any length, which can include coded and non-coded amino acids, chemically or biochemically modified or derivatized amino acids, and polypeptides having modified peptide backbones. The term includes fusion proteins, including, but not limited to, fusion proteins with a heterologous amino acid sequence, fusions with heterologous and homologous leader sequences, with or without N-terminal methionine residues; immunologically tagged proteins; fusion proteins with detectable fusion partners, e.g., fusion proteins including as a fusion partner a fluorescent protein, β-galactosidase, luciferase, etc.; and the like. Polypeptides may be of any size, and the term "peptide" refers to polypeptides that are 8-50 residues (e.g., 8-20 residues) in length.

The term "nucleic acid" encompasses DNA, RNA, single stranded or double stranded and chemical modifications thereof. The terms "nucleic acid" and "polynucleotide" are used interchangeably herein.

The term "operably-linked" refers to the association of nucleic acid sequences on a single nucleic acid fragment so that the function of one is affected by the other. For example, a promoter is operably-linked with a coding sequence when it is capable of affecting the expression of that coding sequence (i.e., the coding sequence is under the transcriptional control of the promoter). "Unlinked" means that the associated genetic elements are not closely associated with one another and the function of one does not affect the other.

The phrase "imaging" as used herein refers to methods of detecting the presence of optically detectable signals emitted from a gel microdrop. Imaging may be used provide 2-D as well as 3-D images of a gel microdrop.

The term "induced" with respect to a promoter, is intended to encompass both the initiation of transcription of a downstream nucleic acid sequence, as well as an increase in the rate of transcription of a downstream nucleic acid sequence that is already being transcribed, compared to an uninduced state.

The term "construct" refers to a recombinant nucleic acid sequence, generally recombinant DNA, that has been generated for the purpose of the expression of a specific nucleotide sequence(s), or is to be used in the construction of other recombinant nucleotide sequences. A construct might be present in a vector or in a genome.

The term "recombinant" refers to a polynucleotide or polypeptide that does not naturally occur in a host cell. A recombinant molecule may contain two or more naturally-occurring sequences that are linked together in a way that does not occur naturally. A recombinant cell contains a recombinant polynucleotide or polypeptide.

The term "selective marker" refers to a protein capable of expression in a host that allows for ease of selection of those hosts containing an introduced nucleic acid or vector. Examples of selectable markers include, but are not limited to, proteins that confer resistance to antimicrobial agents (e.g., hygromycin, bleomycin, or chloramphenicol), proteins that confer a metabolic advantage, such as a nutritional advantage on the host cell, as well as proteins that confer a functional or phenotypic advantage (e.g., cell division) on a cell.

The term "expression", as used herein, refers to the process by which a polypeptide is produced based on the nucleic acid sequence of a gene. The process includes both transcription and translation.

The term "introduced" in the context of inserting a nucleic acid sequence into a cell, means "transfection", or "transformation" or "transduction" and includes reference to the incorporation of a nucleic acid sequence into a eukaryotic or prokaryotic cell wherein the nucleic acid sequence may be incorporated into the genome of the cell (e.g., chromosome, plasmid, plastid, or mitochondrial DNA), converted into an autonomous replicon, or transiently expressed (e.g., transfected mRNA).

The term "candidate agents" means oligonucleotides, polynucleotides, siRNA, shRNA genes, gene products, polypeptides, antibodies, small molecules, e.g., up to 2500 Dalton (Da) in size, and other compounds.

The term "coding sequence" refers to a nucleic acid sequence that once transcribed and translated produces a protein, for example, in vivo, when placed under the control of appropriate regulatory elements. A coding sequence as used herein may have a continuous ORF or might have an ORF interrupted by the presence of introns or non-coding sequences. In this embodiment, the non-coding sequences are spliced out from the pre-mRNA to produce a mature mRNA.

The terms "antibody" and "immunoglobulin" are used interchangeably herein. These terms are well understood by those in the field, and refer to a protein consisting of one or more polypeptides that specifically binds an antigen. One form of antibody constitutes the basic structural unit of an antibody. This form is a tetramer and consists of two identical pairs of antibody chains, each pair having one light and one heavy chain. In each pair, the light and heavy chain variable regions are together responsible for binding to an antigen, and the constant regions are responsible for the antibody effector functions.

The recognized immunoglobulin polypeptides include the kappa and lambda light chains and the alpha, gamma ($IgG_1$, $IgG_2$, $IgG_3$, $IgG_4$), delta, epsilon and mu heavy chains or equivalents in other species. Full-length immunoglobulin "light chains" (of about 25 kDa or about 214 amino acids) comprise a variable region of about 110 amino acids at the $NH_2$-terminus and a kappa or lambda constant region at the COOH-terminus. Full-length immunoglobulin "heavy chains" (of about 50 kDa or about 446 amino acids), similarly comprise a variable region (of about 116 amino acids) and one of the aforementioned heavy chain constant regions, e.g., gamma (of about 330 amino acids).

The terms "antibodies" and "immunoglobulin" include antibodies or immunoglobulins of any isotype, fragments of antibodies which retain specific binding to antigen, including, but not limited to, Fab, Fv, scFv, and Fd fragments, chimeric antibodies, humanized antibodies, single-chain antibodies, and fusion proteins comprising an antigen-binding portion of an antibody and a non-antibody protein. The antibodies may be detectably labeled, e.g., with a radioisotope, an enzyme which generates a detectable product, a fluorescent protein, and the like. The antibodies may be further conjugated to other moieties, such as members of specific binding pairs, e.g., biotin (member of biotin-avidin specific binding pair), and the like. The antibodies may also be bound to a solid support, including, but not limited to, polystyrene plates or beads, and the like. Also encompassed by the term are Fab', Fv, F(ab')$_2$, and or other antibody fragments that retain specific binding to antigen, and monoclonal antibodies.

Antibodies may exist in a variety of other forms including, for example, Fv, Fab, and (Fab')$_2$, as well as bi-functional (i.e. bi-specific) hybrid antibodies (e.g., Lanzavecchia et al., Eur. J. Immunol. 17, 105 (1987)) and in single chains (e.g., Huston et al., Proc. Natl. Acad. Sci. U.S.A., 85, 5879-5883 (1988) and Bird et al., Science, 242, 423-426 (1988), which are incorporated herein by reference). (See, generally, Hood et al., "Immunology", Benjamin, N.Y., 2nd ed. (1984), and Hunkapiller and Hood, Nature, 323, 15-16 (1986),).

An immunoglobulin light or heavy chain variable region consists of a "framework" region (FR) interrupted by three hypervariable regions, also called "complementarity determining regions" or "CDRs". The extent of the framework region and CDRs have been precisely defined (see, "Sequences of Proteins of Immunological Interest," E. Kabat et al., U.S. Department of Health and Human Services, (1991)). The numbering of all antibody amino acid sequences discussed herein conforms to the Kabat system. The sequences of the framework regions of different light or heavy chains are relatively conserved within a species. The framework region of an antibody, that is the combined framework regions of the constituent light and heavy chains, serves to position and align the CDRs. The CDRs are primarily responsible for binding to an epitope of an antigen.

Chimeric antibodies are antibodies whose light and heavy chain genes have been constructed, typically by genetic engineering, from antibody variable and constant region genes belonging to different species. For example, the variable segments of the genes from a rabbit monoclonal antibody may be joined to human constant segments, such as gamma 1 and gamma 3. An example of a therapeutic chimeric antibody is a hybrid protein composed of the variable or antigen-binding domain from a rabbit antibody and the constant or effector domain from a human antibody (e.g., the anti-Tac chimeric antibody made by the cells of A.T.C.C. deposit Accession No. CRL 9688), although other mammalian species may be used.

As used herein, the term "humanized antibody" or "humanized immunoglobulin" refers to an non-human (e.g., mouse or rabbit) antibody containing one or more amino acids (in a framework region, a constant region or a CDR, for example) that have been substituted with a correspondingly positioned amino acid from a human antibody. In general, humanized antibodies produce a reduced immune response in a human host, as compared to a non-humanized version of the same antibody.

It is understood that the humanized antibodies designed and produced by the present method may have additional conservative amino acid substitutions which have substantially no effect on antigen binding or other antibody functions. By conservative substitutions is intended combinations such as those from the following groups: gly, ala; val, ile, leu; asp, glu; asn, gln; ser, thr; lys, arg; and phe, tyr. Amino acids that are not present in the same group are "substantially different" amino acids.

The term "specific binding" refers to the ability of an antibody to preferentially bind to a particular analyte that is present in a homogeneous mixture of different analytes. In certain embodiments, a specific binding interaction will discriminate between desirable and undesirable analytes in a sample, in some embodiments more than about 10 to 100-fold or more (e.g., more than about 1000- or 10,000-fold).

In certain embodiments, the affinity between a capture agent and analyte when they are specifically bound in a capture agent/analyte complex is characterized by a $K_D$ (dissociation constant) of less than $10^{-6}$M, less than $10^{-7}$ M, less than $10^{-8}$ M, less than $10^{-9}$ M, less than $10^{-9}$ M, less than $10^{-11}$ M, or less than about $10^{-12}$ M or less.

As used herein the term "isolated", refers to an reagent of interest that is at least 60% free, at least 75% free, at least 90% free, at least 95% free, at least 98% free, and even at least 99% free from other components with which the reagent is associated with prior to purification.

Description of Exemplary Embodiments

Before the present subject invention is described further, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range is encompassed within the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a", "and", and "the" include plural referents unless the context clearly dictates otherwise. Thus, for example, reference to "a cell" includes a plurality of cells and reference to "a candidate agent" includes reference to one or more candidate agents and equivalents thereof known to those skilled in the art, and so forth. It is further noted that the claims may be drafted to exclude any optional element. As such, this statement is intended to serve as antecedent basis for use of such exclusive terminology as "solely", "only" and the like in connection with the recitation of claim elements, or use of a "negative" limitation.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

Gel Microdrop Compositions

As noted above, a gel microdrop composition is provided. In certain embodiments, the gel microdrop composition contains a polymer matrix, an effector particle that releases an effector molecule into the polymer matrix, a first reporter particle that emits a first optically detectable signal and a second reporter particle that emits a second optically detectable signal that is distinguishable from the first optically detectable signal, where the effector particle and said first and second reporter particles are encapsulated by the polymer matrix. Methods of screening that employ the gel microdrop composition and methods of making the gel microdrop composition are also disclosed.

Figure 1:
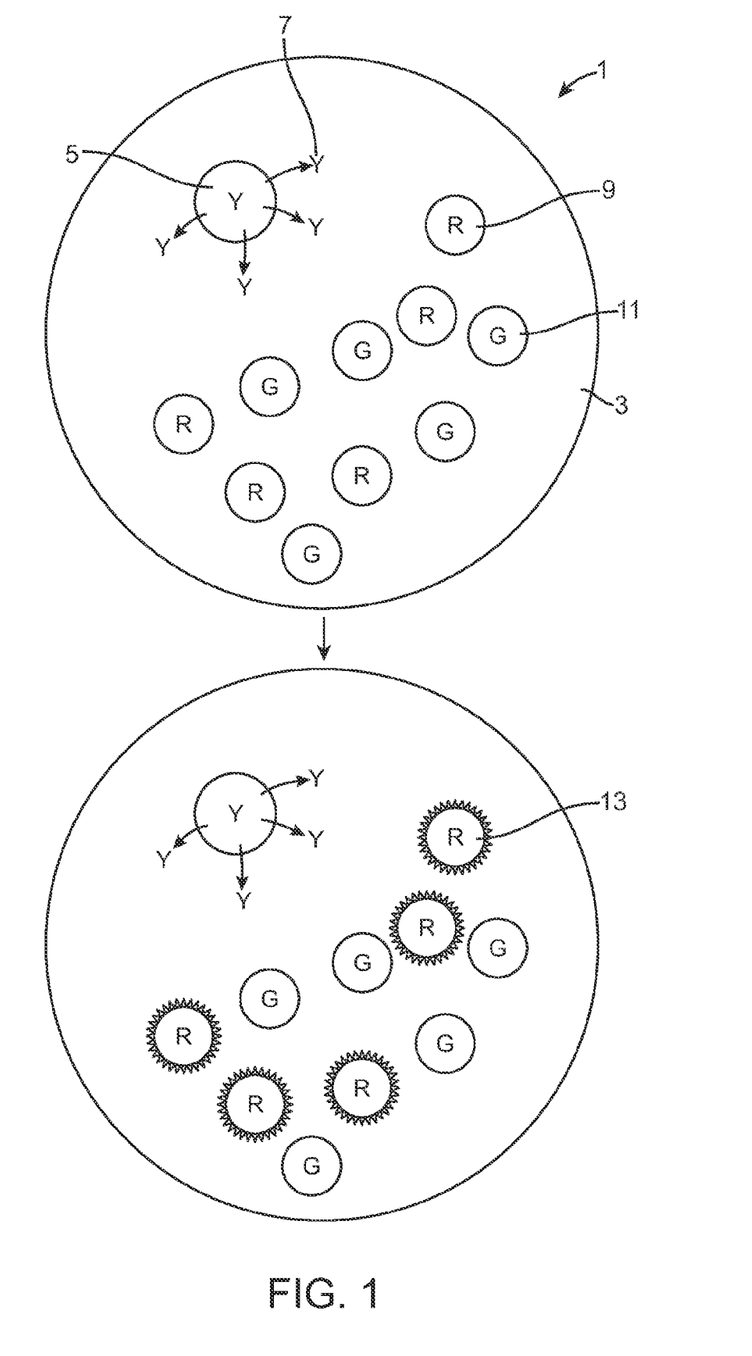
FIG. 1 schematically illustrates certain aspects of a subject microdrop composition and its method of use.

With reference to FIG. 1, a subject gel microdrop composition 1 contains encapsulating polymer matrix 3, effector particle 5, a first reporter particle 9 and a second reporter particle 11. As shown in FIG. 1, effector particle 5 releases an effector molecule 7 ("Y") into the polymer matrix. As noted above, the first reporter particle 9 emits a first optically detectable signal ("R") and the second reporter particle 11 emits a second optically detectable signal ("G") that is distinguishable (i.e., independently detectable) from the first optically detectable signal. As will be described in greater detail below, the first and second reporter particles provide a readout for a biological activity of the effector molecule. In the embodiment shown in FIG. 1, release of effector molecule 7 changes an optically detectable signal localized with one of the first and second reporter particles, relative to a control gel microdrop that does not contain the effector particle. For example and as shown in FIG. 1, release of effector molecule 7 produces altered first reporter particles 13 to produce an altered optically detectable signal. The altered optically detectable signal may be due to: a) labeling of the effector molecule that is bound to the surface of a reporter particle with a third optically detectible signal; b) an increase or decrease in expression, or a change in the localization, of a reporter protein produced by a reporter particle, if the reporter particle is a cell; or c) an increase in uptake of a dye by a reporter particle, if the reporter particle is a cell, for example. As will be described in greater detail below, the reporter particles are different not only because they emit different optically detectable signals, but also because one reporter particle acts as either a positive or negative control for the other reporter particle. For example, the first reporter particle may contain a first antigen on its surface and the second reporter particle may contain a second antigen on its surface, and binding of an effector molecule to the first reporter particle but not the second reporter particle may indicate that the effector molecule is specific for the antigen on the surface of the first reporter particle. In certain cases, there may be no more than a single effector particle as well as multiple (e.g., in the range of 5-100, such as 5-10) of each of the first and second reporter particles in a subject microdrop composition. In other embodiments, there may be more than a single effector particle as well as multiple of each of the first and second reporter particles in a subject microdrop composition. In certain cases, there ratio between the effector particles to each of the first and second reporter particles in a microdrop composition may be, for example, at least 1:5, 1:10 or 1:20, for example.

As will be described in greater detail below, an effector particle may be a bead or a cell, for example. The effector particle need not produce an optically detectable signal. In certain embodiments, however, an effector particle may produce an optically detectable signal in order to allow its presence to be detected.

An effector molecule may be any type of molecule, e.g., a polynucleotide (for example, an oligonucleotide such as an siRNA or antisense RNA), a polypeptide (e.g., a peptide that may or may not be linked to a sequence that facilitates uptake of the polypeptide into cells), a small molecule (e.g., up to 2500 Daltons in size) or an antibody.

Subject gel microdrops may be in the range of 10 μm to 1000 μm in size, e.g., 50 μm to 100 μm, e.g., 100 μm to 300 μm in size.

In particular embodiments, a subject microdrop may be a member of a library of microdrops, where each microdrop of the library contains a different effector particle (i.e., such that the different effector particles produce different effector molecules), and the same first and second reporter particles. Such a library of microdrops may contain at least 10, at least 100, at least 1,000, at least 10,000 or at least 100,000 up to a million or more members, where each member microdrop contains a different effector particle, where the different effector particles produce different effector molecules. In certain embodiments, the members of the microdrop library may be contained as a mixture of microdrops in a single vessel. In other embodiments, the microdrop library may be present in several different vessels, such as wells of a microtiter plate, where each vessel contains at least 1 and up to 10,000 (e.g., 5-100 or 10-50) microdrops. In these embodiments, the microdrops of a single vessel may be present at a density of about 1,000 to 100,000 microdrops per ml and may be suspended in a medium that prevents the settling of the microdrops. Alternatively, microdrops can be centrifuged or allowed to settle on the bottom of a well in a monolayer, or can settle in multiple layers when high-density arrays are desired. In many cases, the microdrops are immersed in a fluid or medium that is compatible with the composition of the embedded particles. For example, if live cells are used as particles, immersion in an appropriate growth media may be necessary to maintain cellular viability. In one embodiment, the microdrops are suspended in phospate buffered saline, pH7.5, for example. In certain embodiments in which the microdrops contain living cells, the microdrops may be suspended in a medium that permits the long term survival of the cells.

Effector Particles

As noted above, an effector particle may be, for example, a cell or a bead. If the effector particle is a cellular effector particle then the effector molecule may be a polypeptide secreted by the cell, i.e., an effector polypeptide. In a particular embodiment, the different members of a library of microdrops may contain cells that secrete different effector polypeptides, where each member of the microdrop library, on average, contains a single effector particle and each effector particle of the library produces a different polypeptide.

Cellular Effector Particles

In one exemplary embodiment, the effector molecules may be a polypeptide secreted by a cell. The polypeptide may be of any sequence (e.g., of random sequence, or may be encoded by cDNA), of any length (e.g., in the range of 10 to 1,000 or more amino acids) from any source (e.g., of mammalian or bacterial origin) and, in certain embodiments may be conformationally constrained. A library of cellular effector particles may, in certain embodiments, be made by introducing an expression library (i.e., a library of expression vectors that provide for expression and secretion of polypeptides) into a population of cells to make a cellular library.

Such expression libraries, e.g., cDNA expression libraries, cDNA fragment expression libraries, random peptide libraries, phage display libraries, are well known in the art (see Ausubel and Sambrook, supra) and their construction will not be discussed here in any great detail. In one embodiment, a polypeptide is expressed in the effector cell using an expression cassette containing a nucleic acid sequence encoding the polypeptide. Expression cassettes, including suitable promoters (e.g., inducible promoters) terminators, enhancers, translation initiation signals, translational enhancers, are well known in the art, and are discussed in Ausubel, et al, (Short Protocols in Molecular Biology, 3rd ed., Wiley & Sons, 1995) and Sambrook, et al, (Molecular Cloning: A Laboratory Manual, Third Edition, (2001) Cold Spring Harbor, N.Y.). Suitable promoters include SV40 elements, as described in Dijkema et al., EMBO J. (1985) 4:761; transcription regulatory elements derived from the LTR of the Rous sarcoma virus, as described in Gorman et al., Proc. Nat'l Acad. Sci USA (1982) 79:6777; transcription regulatory elements derived from the LTR of human cytomegalovirus (CMV), as described in Boshart et al., Cell (1985) 41:521; hsp70 promoters, (Levy-Holtzman, R. and I. Schechter (Biochim. Biophys. Acta (1995) 1263: 96-98) Presnail, J. K. and M. A. Hoy, (Exp. Appl. Acarol. (1994) 18: 301-308)) and the like. In addition, the expression cassette may be engineered to provide for secretion of the polypeptide from the host cell. As such, the expression cassette may encode a fusion protein comprising a signal peptide (otherwise known as a secretion signal) and the polypeptide, where the signal peptide directs the polypeptide to the cells' secretion pathway. Signal peptides suitable for use in any a variety of different cells, including mammalian, fungal and bacterial cells, are well known.

The expression cassette may be linear, or encompassed in a circular vector, which may further comprise a selectable marker. Suitable vectors, e.g., viral and plasmid vectors, and selectable markers are well known in the art and discussed in Ausubel, et al, (Short Protocols in Molecular Biology, 3rd ed., Wiley & Sons, 1995) and Sambrook, et al, (Molecular Cloning: A Laboratory Manual, Third Edition, (2001) Cold Spring Harbor, N.Y.). A variety of different genes have been employed as selectable markers, and the particular gene employed in the subject vectors as a selectable marker is chosen primarily as a matter of convenience. Known selectable marker genes include: the thimydine kinase gene, the dihydrofolate reductase gene, the xanthine-guanine phosporibosyl transferase gene, CAD, the adenosine deaminase gene, the asparagine synthetase gene, the antibiotic resistance genes, e.g., tetr, ampr, Cmr or cat, kanr or neor (aminoglycoside phosphotransferase genes), the hygromycin B phosphotransferase gene, and the like. Vectors may provide for integration into the host cell genome, or may be autonomous from the host cell genome.

Expression cassettes may be introduced into a host cell using a variety of methods, including viral infection, transfection, conjugation, protoplast fusion, electroporation, particle gun technology, calcium phosphate precipitation, direct microinjection, viral vector delivery, and the like. The choice of method is generally dependent on the type of cell being transformed and the circumstances under which the transformation is taking place (i.e., in vitro). A general discussion of these methods can be found in Ausubel, et al, Short Protocols in Molecular Biology, 3rd ed., Wiley & Sons, 1995. In some embodiments lipofectamine and calcium mediated gene transfer technologies are used. Methods for introducing circular nucleic acids are also well known in the art and discussed in Ausubel, above.

In one embodiment, the effector polypeptide may be an antibody secreted by an antibody-producing cell. Such a cell may be involved in a mammalian immune response, such as a B-lymphocyte or its progeny including the plasma cell, and usually produce immunoglobulin heavy and light chains that have been "naturally paired" by the immune system of a host animal. These cells may either secrete antibodies (antibodysecreting cells) or maintain antibodies on the surface of the cell without secretion into the cellular environment. Also encompassed by the term antibody producing cell is a hybridoma cell that expresses an antibody.

An antibody-producing cell may be obtained from an animal which has not been immunized with a selected antigen, which has been immunized with a selected antigen, or which has developed an immune response to an antigen as a result of disease or condition. Animals may be immunized with a selected antigen using any of the techniques well known in the art suitable for generating an immune response (see Handbook of Experimental Immunology D. M. Weir (ed.), Vol 4, Blackwell Scientific Publishers, Oxford, England, 1986). Within the context of this description, the phrase "selected antigen" includes any substance to which an antibody may be made, including, among others, proteins, carbohydrates, inorganic or organic molecules, transition state analogs that resemble intermediates in an enzymatic process, nucleic acids, cells, including cancer cells, cell extracts, pathogens, including living or attenuated viruses, bacteria and the like. As will be appreciated by one of ordinary skill in the art, antigens which are of low immunogenicity may be accompanied with an adjuvant or hapten in order to increase the immune response (for example, complete or incomplete Freund's adjuvant) or with a carrier such as keyhole limpet hemocyanin (KLH).

Many warm-blooded animals, in particular mammals such as humans, rabbits, mice, rats, sheep, cows or pigs and ayes such as chickens and turkeys, may be used in order to obtain antibody-producing cells. Procedures for immunizing animals are well known in the art, and are described in Harlow et al. (*Antibodies: A Laboratory Manual*, First Edition (1988) Cold Spring Harbor, N.Y.). Antibody-producing cells may also be obtained from a subject which has generated the cells during the course of a selected disease or condition. For instance, antibody-producing cells from a human with a disease of unknown cause, such as rheumatoid arthritis, may be obtained and used in an effort to identify antibodies which have an effect on the disease process or which may lead to identification of an etiological agent or body component that is involved in the cause of the disease. Similarly, antibody-producing cells may be obtained from subjects with disease due to known etiological agents such as malaria or AIDS. These antibody-producing cells may be derived from the blood, lymph nodes or bone marrow, as well as from other diseased or normal tissues. Antibody-producing cells may also be prepared from blood collected with an anticoagulant such as heparin or EDTA. The antibody-producing cells may be further separated from erythrocytes and polymorphs using standard procedures such as centrifugation with Ficoll-Hypaque (Pharmacia, Uppsula, Sweden). Antibody-producing cells may also be prepared from solid tissues such as lymph nodes or tumors by dissociation with enzymes such as collagenase and trypsin in the presence of EDTA.

Antibody-producing cells may also be obtained by culture techniques such as in vitro immunization. Examples of such methods are described Reading in Methods in Enzymology (21:18-33 J. J. Langone, H. H. van Vunakis (eds.), Academic Press Inc., N.Y.; 1986). Briefly, a source of antibody-producing cells, such as a suspension of spleen or lymph node cells, or peripheral blood mononuclear cells are cultured in medium such as RPMI 1640 with 10% fetal bovine serum and a source of the substance against which it is desired to develop antibodies. This medium may be additionally supplemented with amounts of substances known to enhance antibody-forming cell activation and proliferation such as lipopolysaccharide or its derivatives or other bacterial adjuvants or cytokines such as IL-1, IL-2, IL-4, IL-5, IL-6, GM-CSF, and IFN-.gamma. To enhance immunogenicity, the selected antigen may be coupled to the surface of cells, for example, spleen cells, by conventional techniques such as the use of biotin/avidin.

Once a suitable animal containing an antibody-producing cell has been identified or produced, spleen, lymph node or bone marrow tissue is typically removed, and a cell suspension of antibody-producing cells is prepared using techniques well known in the art. In some embodiments, this suspension is a single cell suspension, techniques for the preparation of which are well known in the art, e.g., Harlow et al. (*Antibodies: A Laboratory Manual*, First Edition (1988) Cold Spring Harbor, N.Y.).

Antibody-producing cells may be enriched from the single cell suspension by methods based upon the size or density of the antibody-forming cells relative to other cells. An example of the use of Percoll to separate cells according to density is described by van Mourik and W. P. Zeizlmaker in Methods in Enzymology 121:174-182 (J. J. Langone, H. H. van Vunakis (eds.), Academic Press Inc., N.Y.). Gradients of varying density of solutions of bovine serum albumin can also be used to separate cells according to density. (See N. Moav and T. N. Harris, J. Immunol 105:1512, 1970; see also Raid, D. J. in SELECTED METHODS IN CELLULAR IMMUNOLOGY, B. Mishell and S. Shiigi (eds.), W. H. Freeman and Co., San Francisco, 1987). Carroll (Journal of Immunological Methods 2005 296:171-8) Bohm (Journal of Immunological Methods 2005 307: 13-23); Carroll (Expert opinion on biological therapy 2004 4:1821-9) also describe methods for separating antibody-producing cells. Antibody-producing cells may also be enriched and plated using other methods. Exemplary antibody-producing cell enrichment methods include performing flow cytometry (FACS) of cell populations obtained from rabbit spleen, bone marrow, lymph node or other lymph organs, e.g., through incubating the cells with labeled anti-rabbit IgG and sorting the labeled cells using a FACSVantage SE cell sorter (Becton-Dickinson, San Jose, Calif.). In many embodiments, single or nearly single antibody-producing cells are deposited in microtiter plates. If the FACS system is employed, sorted cells may be deposited after enrichment directly into a microtiter plate. Unenriched cells, or cells enriched by any of the above methods may be deposited into a microtiter plate at a limiting dilution (Harlow et al. (*Antibodies: A Laboratory Manual*, First Edition (1988) Cold Spring Harbor, N.Y.) to ensure single cell deposition.

In certain embodiments, the antibody-producing cells are or are not further selected based on the affinity of the antibodies that are expressed by the antibody-producing cells. As such, in certain cases, antibody producing cells may be used directly after enrichment, and may not be subject to any further purification or selection based on the reactivity or specificity of the antibodies being expressed by the antibody producing cell. In some embodiments, the antibody-producing cells are of "unknown" specificity because the antigen (i.e. the protein, pathogen, peptide, cell, cell extract, nucleic acid, carbohydrate etc.) to which the antibodies of the antibody producing cells bind is not determined prior to screening.

Optionally, the antibody-producing cells are then cultured (i.e. grown in media that supports at least one, at least 5 or at least 10 or more cell divisions of the cell) by methods known to one of skill in the art after they have been deposited (see e.g. WO 01/55216). As such, a microdrop composition may be obtained from the progeny of a single antibody-producing cell. In certain embodiments, however, the antibody producing cells are not cultured before they are used into a microdrop.

The effector cell of a microdrop may be of any cell type, including mammalian, bacterial, fungal, plant, avian, fish, amphibian, and reptile cells.

Bead Effector Particles

In another exemplary embodiment, the effector particle is a bead, where the effector molecule may be linked to the bead via a cleavable linker. Upon exposure of a bead effector particle to a condition that cleaves the linker, the effector molecule is released from the bead and can diffuse to reporter particles.

Beads can range in size from 20 nM to 200 μM or larger, and may be made of polystyrene, but other materials such as polymethylmethacrylate (PMMA), polyvinyltoluene (PVT), styrene/butadiene (S/B) copolymer, styrene/vinyltoluene (S/VT) are also used. Densities can range from 1.01 to 1.50 g/ml. Beads can be made to display a variety of chemically functional groups on their surface. Reactive groups commonly used include carboxyl, amino, aldehyde, hydroxyl, epoxy, and chloromethyl (See, e.g., U.S. Pat. Nos. 4,217,338, 5,326,692, 5,786,219, 4,717,655, 7,445,8445,573,909 and 6,023,540) To these reactive groups other types of linkers can be attached. Beads as described above can be obtained commercially from numerous sources including Molecular Probes (Invitrogen), Bangs Labs, and Polymicroshperes, Inc.

A bead effector particle may contain capture agents that are cleavably linked (i.e., cleavably bound, indirectly or directly) to the surface of a bead. In some embodiments, the capture agent is bound to the substrate via a cleavable linker.

Cleavable linkers that may be employed in the subject effector bead include electrophilically cleavable linkers, nucleophilically cleavable linkers, photocleavable linkers, metal cleavable linkers, electrolytically-cleavable, and linkers that are cleavable under reductive and oxidative conditions. Such linkers are described in great detail by Guillier et al (Chem. Rev. 2000 1000:2091-2157), which disclosure is incorporated by reference in its entirety.

Suitable cleavable sites include, but are not limited to, the following: base-cleavable sites such as esters, particularly succinates (cleavable by, for example, ammonia or trimethylamine), quaternary ammonium salts (cleavable by, for example, diisopropylamine) and urethanes (cleavable by aqueous sodium hydroxide); acid-cleavable sites such as benzyl alcohol derivatives (cleavable using trifluoroacetic acid), teicoplanin aglycone (cleavable by trifluoroacetic acid followed by base), acetals and thioacetals (also cleavable by trifluoroacetic acid), thioethers (cleavable, for example, by HF or cresol) and sulfonyls (cleavable by trifluoromethane sulfonic acid, trifluoroacetic acid, thioanisole, or the like); nucleophile-cleavable sites such as phthalamide (cleavable by substituted hydrazines), esters (cleavable by, for example, aluminum trichloride); and Weinreb amide (cleavable by lithium aluminum hydride); and other types of chemically cleavable sites, including phosphorothioate (cleavable by silver or mercuric ions) and diisopropyldialkoxysilyl (cleavable by fluoride ions). Other cleavable sites will be apparent to those skilled in the art or are described in the pertinent literature and texts (e.g., Brown (1997) Contemporary Organic Synthesis 4(3); 216-237).

In particular embodiments, a photocleavable linker (e.g., a uv-cleavable linker) may be employed. Suitable photocleavable linkers for use in a subject sensor include ortho-nitrobenzyl-based linkers, phenacyl linkers, alkoxybenzoin linkers, chromium arene complex linkers, NpSSMpact linkers and pivaloylglycol linkers, as described in Guillier et al, supra.

As is known in the art, a molecule can be tethered to a substrate using a suitable linking agent (e.g., a suitable ortho-nitrobenzyl-based linking agent) that generally possesses the following features, in order: a tag for linking to a substrate, a spacer moiety, a cleavable linker and a reactive group. The tag may be an affinity tag, e.g., a biotin group or the like, or a reactive moiety (e.g. a carboxy group, an amino group, a halo group, a tosylate group, a mesylate group, a reactive hydroxyl groups or metal oxide) that can react with suitable sites (e.g., alcohols, amino nucleophiles, thiol nucleophiles or silane groups on the surface of a substrate to produce a covalent bond between the substrate and the linker. The spacer may contain an unreactive alkyl chain, e.g., containing 3-12 carbon atoms (e.g., 5-aminocaproic acid) and the cleavable linker may be chosen as containing appropriate chemistry (see above). The reactive group generally reacts with the effector molecule and forms a covalent bond therewith. The reactive group is selectively reactive with particular chemical groups in the capture agent.

Suitable reactive groups include halogens (that are sulhydryl reactive), N-hydroxysuccinimide (NHS)-carbonate (that are amine-reactive) and N,N-diisopropyl-2-cyanoethyl phosphoramidite (that are hydroxyl-reactive), and several other reactive groups are known in the art and may be readily employed in the instant methods.

In particular embodiments, it is desirable to cleave a cleavably-bound effector molecule at a bond that releases a "native" form of the molecule, i.e., a molecule that has an identical molecular structure to that of the same molecule prior to becoming linked to the cleavable linker. In these embodiments, a photocleavable ortho-nitrobenzyl NHS linking agent may be employed. In these embodiments, at least one amino group (NH2) of a molecule is reacted with the NHS group of the linking agent to produce a molecule in which the linker and the capture agent are covalently linked via a uv-cleavable bond. Upon subjecting this molecule to uv light, the uv-cleavable bond is cleaved, and the molecule (having its original amino group) is released. The released molecule has an identical molecular structure to the capture agent reacted with the linking agent. Exemplary photocleavable ortho-nitrobenzyl NHS linkers may be cleaved by uv light.

Exemplary linking agents that may be employed in the subject methods are described in Guillier et al, supra and Olejnik et al (Methods in Enzymology 1998 291:135-154), and further described in U.S. Pat. No. 6,027,890; Olejnik et al (Proc. Natl. Acad Sci, 92:7590-94); Ogata et al. (Anal. Chem. 2002 74:4702-4708); Bai et al (Nucl. Acids Res. 2004 32:535-541); Zhao et al (Anal. Chem. 2002 74:4259-4268); and Sanford et al (Chem Mater. 1998 10:1510-20), and are purchasable from Ambergen (Boston, Mass.; NHS-PC-LC-Biotin), Link Technologies (Bellshill, Scotland), Fisher Scientific (Pittsburgh, Pa.; PIERCE EZ-LINK™ NHS-PC-LC-Biotin) and Calbiochem-Novabiochem Corp. (La Jolla, Calif.).

As would be recognized by one of skill in the art, effector molecules can be pre-made (e.g., synthesized by a machine or made by recombinant means) and then bound to the linker. Alternatively, capture agents that are already covalently bound to a linker may be made using synthetic means (e.g., using a machine).

In one embodiment, an NHS and ortho-nitrobenzyl group-containing biotinylated linker agent is combined with a primary amine-group containing effector molecule (e.g., a polypeptide or aminated nucleic acid) at pH 7-9. The amine reacts with the NHS group by nucleophilic attack, and the by-product of the reaction, N-hydroxysuccinimide, is released. The resulting biotinylated photocleavable linker-containing effector molecule may be stored in DMF or DMSO protected from light and moisture at −20° C., indefinitely.

The biotinylated photocleavable linker-containing effector molecule may be contacted with a bead coated in streptavidin or avidin and incubated a suitable amount of time (e.g., 15-30 minutes) in binding buffer with gentle mixing. The biotinylated photocleavable linker-containing effector molecule thereby becomes bound to the streptavidin. The bound effector molecule may be washed in phosphate buffered saline (PBS) or other suitable buffer, and the bead may then be employed.

A non-biotinylated linker agent may be attached to a bead via reactive functional moieties on both the substrate and the linker. The reactive moiety of the linker agent (e.g., an amino group, a sulfide group, etc.) can be reacted with a suitable site (e.g., a carboxylic acid group, a reactive-halogen, etc.) on the surface of a bead to produce a covalent bond between the substrate and the non-biotinylated photocleavable linker-containing effector molecule. The bead with the bound effector molecule may then be employed.

The cleavably bound capture agent may be cleaved from the substrate by exposing the substrate to light of 300-370 nm wavelength, e.g., 365 nm, at a suitable intensity, e.g., 1.2 mW/cm$^2$.

In an alternative embodiment, a photoacid generator (PAG) material may be employed as a cleavage agent. Such PAGs are known in the art (see, e.g., the world wide website of Sigma-Aldrich) and include N-hydroxyphthalimide trifluoromethanesulfonate, 2-Naphthyl diphenylsulfonium triflate, bis(4-tert-butylphenyl)iodonium perfluoro-1-butanesulfonate, bis(4-tert-butylphenyl)iodoniump-toluenesulfonate, bis(4-tert-butylphenyl)iodonium trifluoromethanesulfonate, (4-Bromophenyl)diphenylsulfonium trifluoromethanesulfonate, (tert-Butoxycarbonylmethoxynaphthyl)-diphenylsulfonium triflate, and many others. In this embodiment, a PAG may be present in the flowstream of the sensor (e.g., mixed with sample). When UV light is directed at an area (i.e., a localized region) of this flow stream, protons are generated within the lighted area and the pH of the area drops. Any pH-sensitive material present in the area (e.g., sensitive esters or pH-sensitive binding) would be subject to modification (i.e., cleavage, hydrolysis, binding-disruption). For example, photo-induced acid generation produced by PAG is sufficient to cleave an ester bond to release a effector molecule bound to a bead by such a bond.

In a further embodiment, a effector molecule may be bound to a substrate through an electrolytically-cleavable linker. In this case, the effector molecule can be released via electrolytic means. Acid-cleavable linkers may also be cleaved by a change in pH. Guidance for performing such method are readily adapted from Donner et al (Biochemica 4, 2003, a publication of Roche Applied Science, Indianapolis, Ind.).

The effector molecule may be any molecule, including synthetic, semi-synthetic, naturally-occurring inorganic and organic molecules. Candidate agents include those found in large libraries of synthetic or natural compounds. For example, synthetic compound libraries are commercially available from Maybridge Chemical Co. (Trevillet, Cornwall, UK), ComGenex (South San Francisco, Calif.), and MicroSource (New Milford, Conn.). Alternatively, libraries of natural compounds in the form of bacterial, fungal, plant and animal extracts are available from Pan Labs (Bothell, Wash.) or are readily producible.

Candidate agents may be small organic or inorganic compounds having a molecular weight of more than 50 and less than about 2,500 Da. Candidate agents may comprise functional groups necessary for structural interaction with proteins, particularly hydrogen bonding, and may include at least an amine, carbonyl, hydroxyl or carboxyl group, and may contain at least two of the functional chemical groups. The candidate agents may comprise cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs or combinations thereof.

Candidate agents are obtained from a wide variety of sources including libraries of synthetic or natural compounds. For example, numerous means are available for random and directed synthesis of a wide variety of organic compounds and biomolecules, including expression of randomized oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs. New potential therapeutic agents may also be created using methods such as rational drug design or computer modeling.

Reporter Particles

As noted above, the first and second reporter particles in a subject microdrop produce spectrally distinguishable signals and contain at least one molecular difference so that one reporter particle serves as a positive or negative control for the other particle to determine if the effect of the effector molecule is specific. As noted above, the first and second reporter particles may be beads or cells, for example.

If the first and second reporter particles are beads, then they may be labeled using distinguishable fluorescent dyes, although other labeling systems, e.g., quantum dots, etc, may be employed.

Beads can be colored with a variety of organic or fluorescent dyes. Dye molecules can be attached to the bead surface, or more commonly, trapped in the interior of the particle, leaving the surface available for the attachment of biomolecules. (See, e.g., many of the references cited above, Kallar et al, Exp. Hematol. 2002 20 1227-1237, Fulton et al Clinical Chemistry 1997 1749-1756 and The Vanderbilt Latex Handbook, R. Mausser) Suitable dyes include: xanthene dyes, e.g. fluorescein and rhodamine dyes, such as fluorescein isothiocyanate (FITC), 6-carboxyfluorescein (commonly known by the abbreviations FAM and F), 6-carboxy-2',4',7',4,7-hexachlorofluorescein (HEX), 6-carboxy-4', 5'-dichloro-2', 7'-dimethoxyfluorescein (JOE or J), N,N,N',N'-tetramethyl-6-carboxyrhodamine (TAMRA or T), 6-carboxy-X-rhodamine (ROX or R), 5-carboxyrhodamine-6G (R6G$^5$ or G$^5$), 6-carboxyrhodamine-6G (R6G$^6$ or G$^6$), and rhodamine 110; cyanine dyes, e.g. Cy3, Cy5 and Cy7 dyes; coumarins, e.g umbelliferone; benzimide dyes, e.g. Hoechst 33258; phenanthridine dyes, e.g. Texas Red; ethidium dyes; acridine dyes; carbazole dyes; phenoxazine dyes; porphyrin dyes; polymethine dyes, e.g. cyanine dyes such as Cy3, Cy5, etc; BODIPY dyes and quinoline dyes. Specific fluorophores of interest that are commonly used in some applications include: pyrene, coumarin, diethylaminocoumarin, FAM, fluorescein chlorotriazinyl, R110, eosin, JOE, R6G, tetramethylrhodamine, TAMRA, lissamine, ROX, napthofluorescein, Texas red, napthofluorescein, Cy3, and Cy5, etc.

Suitable distinguishable fluorescent label pairs useful in the subject methods include Cy-3 and Cy-5 (Amersham Inc., Piscataway, N.J.), Quasar 570 and Quasar 670 (Biosearch Technology, Novato Calif.), Alexafluor555 and Alexafluor647 (Molecular Probes, Eugene, Oreg.), BODIPY V-1002 and BODIPY V1005 (Molecular Probes, Eugene, Oreg.), POPO-3 and TOTO-3 (Molecular Probes, Eugene, Oreg.), and POPRO3 TOPRO3 (Molecular Probes, Eugene, Oreg.). Further suitable distinguishable detectable labels may be found in Kricka et al. (Ann Clin Biochem. 39:114-29, 2002). Beads may also be labeled using fluorescent proteins.

The first and second reporter beads may each contain a moiety, e.g., a protein, that is bound to the reporter beads, where the first and second reporter beads have different moieties bound thereto. In one embodiment, one of the reporter beads contains a target moiety, e.g., a moiety to which an effector molecule may bind such as a first polypeptide, whereas the other of the reporter beads contains a control moiety, e.g., a moiety to which the effector molecule should not bind, such as a second polypeptide that is different to the first polypeptide. In other words, the first reporter beads may have a surface-bound target moiety that may bind to an effector molecule, whereas the second reporter bead may contain a surface-bound target moiety that does not bind to the effector molecule, where the second reporter bead acts as a control for the first reporter bead. Binding of an effector molecule to the first reporter bead but not the second reporter bead indicates that the effector molecule specifically binds to the moiety presented on the first reporter bead. Illustrated by example, one reporter particle may have a target protein on its surface, and the other may contain a mutant version of the protein, and, as will be described in greater detail below, the two reporter particles may be used to screen for, for example, an effector molecule such as an antibody, that binds to the target protein rather than the mutant protein.

In certain cases, one of the reporter particles may contain the antigen used to immunize an animal that produces antibody-producing cells, as described above. In this embodiment, a microdrop may contain an effector particle that is an antibody-producing cell obtained from an animal immunized by a polypeptide, and first and second reporter particles, one of which contains the polypeptide. Binding of an antibody produced by the antibody-producing cell to the reporter particle containing the polypeptide but not the other reporter particle indicates that the antibody specifically binds to the polypeptide. In other embodiments, the reporter particles may be living cells, in which case the distinguishable optically detectable signals may be from, for example: a) distinguishable vital dyes loaded into the cells prior to manufacture of the microdrops, b) differential labeling of cell-surface markers that are differentially expressed by the cells, c) distinguishable reporter proteins produced by the cells, or d) transfected beads, quantum dots, or metallic particles. These particles are detected and decoded within each cell via microscopy, thus revealing cell types in a mixed population of reported cells.

In one embodiment, distinguishable reporter proteins may be employed, which reporter proteins may be from a cyan fluorescent protein, a yellow fluorescent protein, a green fluorescent protein, a red fluorescent protein, a blue fluorescent protein, or any mutant thereof, including mutants of ECFP, EYFP, EGFP, ERFP, EBFP, obtained by enhancing the fluorescence intensity. Such reporter proteins may be derived from the fluorescent proteins of *Aequorea, Discoma, Ptilosarcus*, or *Renilla* GFP, for example, which proteins are well known. Alternatively, derivatives based upon the luciferase family proteins, most commonly firefly (*Photinus pyralis*) and *Renilla reniformis*, can produce a luminescent signal that is detectable in an microscopy imaging environment. In another embodiment, the reporter gene does not produce a fluorescent or luminescent signal directly, but rather enzymatically converts a non-fluorescent substrate to a fluorescent product. Commonly used enzymes include B-galactosidase, horseradish peroxidase, alkaline phosphatase, B-glucuronidase, B-lactamase, chloramphenicol acetyltransferase. A wide array of substrates for fluorescence and luminescence detection are available commercially (Sigma, Invitrogen). The reporter proteins may encoded by a nucleic acid that is operably linked to a constitutive or inducible promoter. In one embodiment and as will be described in greater detail below, the expression of a reporter protein may be driven by an inducible promoter, where an alteration in the expression of the reporter protein by the effector molecule indicates that the effector molecule modulates expression of the inducible promoter. In another embodiment, the reporter may by produced as a fusion protein, where the fusion protein contains a reporter protein region and a region from a cellular protein.

In another embodiment, the detection molecules are exogenous, being added to the reporter cells during the course of the assay, and do not require the expression of a foreign gene. These detectors may be small molecules that pass freely into living cells and be converted to a detectable product, or not, depending on the physiological state of the cell. Examples include: 1) AFC (Clontech), a dervative of coumarin that becomes fluorescent upon cleavage by caspase, and is indicative of an apoptotic state; 2) Fura-2 for detection of a increase of intracellular calcium, and is indicative of cellular activation; 3) fluorescent nucleotide analogs for the detection of cellular proliferation; 4) the SYTO dyes (Invitrogen) that fluoresce only upon binding DNA, also used for measurement of DNA content and cellular proliferation. In addition to membrane-permeant molecules, large molecules such as antibodies can be labeled and used as probes for cell surface receptors that correlate with certain cellular states, for example, anti-annexin V can be used as a probe for a pre-apoptotic state; and anti-fibronectin present is used as a probe for chemotaxis, detecting fibronectin in the extracellular matrix. Antibody probes can also be used to detect intracellular markers of proliferation, activation, and cell cycle control, including cdc6 protein, HuR, and D cyclins. Use of large molecule probes directed at intracellular targets requires permeablization of the reporter cells.

As for the reporter beads discussed above, the first and second cellular reporter particles may be different to each in some way so that the specificity of an effector molecule can be evaluated by comparing the cellular reporter particles. For example, in one embodiment, one of the reporter cells may contain a cell surface receptor that the other cell lacks, allowing the identification of effector molecules that specifically interact with or modulate signal transduction downstream of the receptor. Cell surface receptors include those of: GD2, EGF-R, CEA, CD52, CD20, Lym-1, CD6, complement activating receptor (CAR), EGP40, VEGF, tumor-associated glycoprotein TAG-72 AFP (alpha-fetoprotein), BLyS (TNF and APOL—related ligand), CA125 (carcinoma antigen 125), CEA (carcinoembrionic antigen), CD2 (T-cell surface antigen), CD3 (heteromultimer associated with the TCR), CD4, CD11 a (integrin alpha-L), CD14 (monocyte differentiation antigen), CD20, CD22 (B-cell receptor), CD23 (low affinity IgE receptor), CD25 (IL-2 receptor alpha chain), CD30 (cytokine receptor), CD33 (myeloid cell surface antigen), CD40 (tumor necrosis factor receptor), CD44v6 (mediates adhesion of leukocytes), CD52 (CAMPATH-1), CD80 (costimulator for CD28 and CTLA-4), complement component C5, CTLA, EGFR, eotaxin (cytokine All), HER2/neu, HER3, HLA-DR, HLA-DR10, HLA ClassII, IgE, GPiib/iiia (integrin), Integrin aVβ3, Integrins a4β1 and a4β7, Integrin β2, IFN-gamma, IL-1β, IL-4, IL-5, IL-6R (IL6 receptor), IL-12, IL-15, KDR (VEGFR-2), lewisy, mesothelin, MUC1, MUC18, NCAM (neural cell adhesion molecule), oncofetal fibronectin, PDG-FβR (Beta platelet-derived growth factor receptor), PMSA, renal carcinoma antigen G250, RSV, E-Selectin, TGFbeta1, TGFbeta2, TNFα, DR4, DR5, DR6, VAP-1 (vascular adhesion protein 1) and VEGF, or the like.

In another embodiment, one of the reporter cells may contain a transcription factor that the other reporter cell lacks, thereby allowing effector molecules that specifically modulate that promoter to be identified. In another embodiment, the first and second reporter cells may contain distinguishable fluorescent reporter proteins that are linked to different promoters, where activation of only one promoter by an effector molecule indicates that the effector molecule specifically modulates that promoter. In another embodiment the first reporter cell co-expresses a protease capable of degrading the fluorescent protein unless the degradation is blocked by a protease inhibitor produced by the effector particle.

The polymer matrix may be e.g., agarose (as described in Weaver, Methods 1991 2:234-247), carrageenan, alginate, alginate-polylysine, collagen, a plant-derived gum, cellulose or a derivatives thereof (e.g., methylcellulose), gelatin, chitosan or an extracellular matrix (ECM), as described by Kleinman (U.S. Pat. No. 4,829,000). Suitable synthetic hydrogels include polyvinyl alcohol, block copolymer of ethylene-vinylalcohol, sodium polystyrene sulfonate, vinyl-methyl-tribenzyl ammonium chloride and polyphosphazene (Cohen, S. et al. J. Anal. Chem. Soc., 112, pp. 7832-7833 (1990)). Powell (Bio/Technology 1990 8:333-337) provides methods for detecting proteins in microdrops using antibodies.

In general terms, a subject gel microdrop may be made by: a) combining: a monomer for a polymer; with an effector particle, a first reporter particle and a second reporter particle as discussed above to produce a particle-containing composition; b) making droplets of the particle-containing composition; and c) polymerizing the monomers of the droplets. Methods for producing related compositions are described in U.S. Pat. Nos. 4,399,219, 4,401,755, 4,409,331, 4,643,968, 4,647,536, 4,801,529, 4,959,301, 6,426,088, 6,586,176, 6,806,058, 7,011,957, 7,297,538 and 7,482,152, as well as Bogen (Toxicology 2001 160: 5-10); Demirci (Lab on a chip 2007 7: 1139-45) Edd (Lab on a chip 2008 8: 1262-4); Gift (Nat Biotechnol 1996 14: 884-7); Gift (Cytometry 2000 39: 243-9); Goguen (Nature 1993 363: 189-90); Gray (Journal of Immunological Methods 1995 182: 155-63; Ling (Lab on a chip 2007 7: 756-62); Macis (J. Neurosci. Methods 2007 161: 88-95); Powell (Biotechnology 1990 8: 333-7); Uludag (Adv. Drug Deliv. Rev. 2000 42: 29-64); Weaver (Nat Med 1997 3:583-5) Weaver (Biotechnology 1991 9: 873-7) and Zengler (Proc. Natl. Acad. Sci. 2002 99: 15681-6), which references are incorporated herein for disclosure of those methods. The methods described in these references may be readily adapted for use herein.

As noted above, a subject microdrop may contain a single effector particle and multiple reporter particles. The number of effector and reporter particles may be controlled by Poisson statistics, as described by Powell et al. and Weaver et al (Biotechnology 1991 9: 873-877) During the emulsification process particles are randomly distributed into the nascent microdrops. Since virtually all of the particles become embedded in microdrops, if the number of particles exceeds the number of microdrops, each microdrop may contain, on average, >1 particle. Likewise, if the number of microdrops exceeds that of the particles, then each microdrop may contain, on average, <1 particle. In general, for some of the methods described herein, it may be desirable to have exactly 1 effector particle per microdrop since this configuration would produce a single type of effector molecule that may act upon reporter particles/cells, and thus generate a result that is more interpretable than if multiple types of effector molecules were present in the microdrop. In some instances, microdrops may contain effector cells that will be allowed to grow over time, resulting in multiple effector cells per microdrop. In this case the cells would be clonal in origin, and hence only produce one type of effector molecule. With respect to the reporter particles, on the other hand, it may be desirable to have multiple members of each type contained within each microdrop. Five to twenty reporter particles per microdrop may be ideal for a statistically significant readout of effector molecule effect. Correct loading of various particle/cell types in microdrops can be confirmed by microscopy.

Method of Screening

A method of screening that employs a subject microdrop is provided. In general terms, the screening method involves detecting an alteration in an optically detectable signal localized with one of the first and second reporter particles in a subject gel microdrop composition, relative to a control gel microdrop that does not contain the same effector particle. In certain embodiments, the method involves detecting an effect of the effector molecule on one of the first or second optically detectable signals. In other embodiments, the method may method involves detecting an effect of the effector molecule on a third optically detectable signal, distinguishable from the first and second optically detectable signals, localized with one of the reporter particles. The third optically detectable signal may be produced by, for example: a) labeling the effector molecule with a third optically detectable label (where, for example, the alteration is a colocalization of the third optically detectable signal produced by the labeled effector molecule with the first or second reporter particles, indicating that the effector molecule binds to one of the first or second reporter particles) or b) a reporter in a cellular reporter particle (where, for example, the alteration is a change in expression or localization of a fluorescent reporter protein produced by the cell, or an increase in a fluorescent dye taken up by the cell). In other words, an alteration may be detected as: a colocalization of a third optically detectable signal with one of the reporter particles, an alteration in a third optically detectable signal that is localized with one or both of the reporter particles (which may, in certain embodiments, indicate that an antibody is bound to a reporter particle), or an alteration in the first or second optically detectable signals, where an alteration may be an increase in signal, a decrease in signal, a change in sub-cellular distribution of a signal, an increase or decrease in area of the signal, etc.

In certain cases, the binding of the effector molecule to a reporter particle may be detected using, for example, a labeled antibody that recognizes the effector molecule. For example, if the effector molecule is an antibody from a first animal species (e.g., mouse), then binding of the mouse antibody to a reporter particle may be detected using a labeled antibody from another animal species (e.g., goat). As such, in one embodiment, the screening method may further include detecting binding of an effector molecule using a labeled antibody that specifically binds to the effector molecule, where the labeled antibody emits third signal, where the third signal is distinguishable from the first and second signals.

In particular embodiments, the reporter cells of a microdrop may be exposed to a condition conducive to a physiological response, and the microdrop is assayed to determine whether the effector particle induces or alters the response. In one exemplary embodiment, the condition may be addition of a ligand for a receptor (where, e.g., the receptor is present on one reporter particle but not the other), or a compound or drug that enhances an apoptotic pathway, for example. In other embodiments, microdrops may be screened for effectors that produce a proliferative effect upon reporter cells, thus the condition may require supporting components in the media such as nutrients and growth factors. In other embodiments, microdrops may be screened for effectors that produce an inhibitory effect on a known signaling pathway. In such a case the condition may be to expose the microdrops to all components necessary to induce a full response, and screen for microdrops containing reporter cells that fail to produce a full response.

In particular embodiments, the individual microdrops of a library may be assessed using fluorescence microscopy using a bandpass filters appropriate for the signals being detected (such as by using a triple bandpass filter for, e.g., DAPI, fluorescein and rhodamine, or whichever fluorescent markers are used). In particular embodiments, the method does or does not employ FACS (fluorescent activated cell sorting). In certain cases is may be important to associate the signal from reporter particles to a particular microdrop and as such in particular embodiments an overlay of a phase or brightfield image will be used to demarcate the boundaries of each microdrop. In other embodiments, it is desirable to screen large numbers (>10 million) of microdrops for rare profiles of effector function. In such a case it may be necessary to perform a primary imaging at low magnification on a single color channel (that of the "$3^{rd}$" signal for example) followed by a secondary imaging, at higher magnification and all color channels, only at selected locations.

In a particular embodiment, a microdrop may be optically sectioned, and an image of the microdrop reconstructed so that each individual reporter particle can be analyzed. In certain cases this may require retaining z-axis information and analyzing microdrops as 3D volumes, or it may require the flattening of a stack of images to generate a single 2D image that has optimal focus for each particle in the microdrop. Imaging tools to perform these manipulations and collect the necessary measurements exist in the form of commercially available software packages from a variety of sources. In certain cases, the results obtained from the first reporter particles may be compared to the results obtained from the second reporter particles to determine if there is a significant difference in a signal compared to reporter particles in a microdrop that contains a different effector particle.

In some embodiments and as described above, the microdrops of a library may be present in different vessels, where there are multiple vessels and each of the vessels contains multiple microdrops. In one example, the microdrops may be in a microtiter plate. In these embodiments, the microdrops of the individual vessels may be analyzed, and the positions of each microdrop in the vessels may be recorded so that an individual microdrop, e.g., a microdrop that contains an effector particle that produces a bioactive effector molecule, can be identified and recovered at later time.

In particular embodiments, a library of microdrops is screened using the method outlined above in order to identify a microdrop that contains an effector particle that produces a bioactive effector molecule. The identity of an effector particle that produces a bioactive effector molecule may be determined by identifying an optical barcode on the particle if the particle is a bead or by analyzing the effector particle from an isolated microdrop, for example. In one embodiment, the identity of a bioactive effector molecule in a microdrop may be determined by recovering the microdrop and amplifying, by PCR for example, a nucleic acid encoding the secreted protein causing the alteration in the optical signal of a reporter particle. In particular embodiments, an indicator cell may be isolated and cultured to produce a cell culture, a portion of which can be used to identify the effector molecule using either biochemical or molecular means, e.g., by PCR or by cDNA cloning, for example.

In the context of identification and recovery of selected microdrops from the imaging environment, a computer guided addressing system may be employed, determining the exact location, in xyz space, of the desired microdrop, and live video visualization of said microdrop. Under these conditions the microdrop can be physically isolated with a manual pipettor or robotically controlled micromanipulator, and transferred to a separate well. In one embodiment, the isolated microdrop contains a single effector cell (B lymhocyte, for example), and mRNA is isolated from this single cell, and cDNA prepared. This cDNA serves as template for a PCR reaction that amplifies the gene encoding the effector molecule of interest (the immunoglobulin V region, for example). In another embodiment, the isolated microdrops are dissolved (with agarase, for example), to release the encapsulated cells, and conditions are met to promote the viability and growth of effector cells for a limited period of time, after which PCR can be performed as described above. In another embodiment, the conditions are met to promote the viability and growth of effector cells indefinitely. In another embodiment, the effector cells are an immortalized type (a hybridoma, for example), so that when isolated microdrops are dissolved and effector cells released, they can be grown indefinitely.

In one exemplary embodiment, the effector particles are beads that are cleavably linked to different candidate agents, where each bead is linked to a different candidate agent and the first and second reporter particles are cells that contain distinguishable fluorescent proteins that are produced using different promoters. The candidate agents are cleaved from the effector particles, and, within a single microdrop, induction of the fluorescent protein in the first reporter particle but not the fluorescent reporter protein of the second report indicates that the candidate agent produced by the effector particle specifically induces the promoter driving the expression of the first reporter protein.

In another exemplary embodiment, the effector particles are beads that are cleavably linked to different candidate agents, where each bead is linked to a different candidate agent and the first and second reporter particles are cells that contain distinguishable fluorescent proteins that are produced using the same promoter. The reporter cells differ in that the first reporter cell contains a particular receptor and the second reporter cell does not contain that receptor. The reporter cells also contain a construct for the expression of a third reporter protein that is distinguishable from the other reporter proteins. The candidate agents are cleaved from the effector particles, and, within a single microdrop, co-localization of the third fluorescent protein with only the first reporter particle indicates that the candidate agent produced by the effector particle specifically induces the promoter driving the expression of the third reporter protein.

In a further exemplary embodiment, the effector particle is an antibody-producing cell and the reporter particles are beads that are distinguishably labeled. The first reporter particle contains a particular receptor bound to its surface, whereas the second reporter particle does not. Colocalization of the antibody with the only first reporter particle indicates that the antibody binds to the receptor.

In another exemplary embodiment, the effector particle is an antibody-producing cell and the reporter particles are cells that are distinguishably labeled by reporter proteins expressed by the cells. The first reporter cells contain an apoptosis-related surface-bound receptor (e.g., the FAS receptor or TNFR), whereas the second reporter cells do not. The microdrops are incubated with a vital dye (e.g., HO342), and an increased dye uptake by the first reporter cells indicates that the antibody produced by the antibody-producing cells induces apoptosis via interaction with the receptor. In an alternative embodiment, the microdrops may be incubated with a vital dye (e.g., HO342) in the presence of a ligand for the apoptosis-related surface-bound receptor (e.g., soluble FAS ligand or TNFα), and an decreased dye uptake by the first reporter cells indicates that the antibody produced by the antibody-producing cells inhibits apoptosis. Further dyes such as PI or 7-AAD may be employed to discriminate between late apoptotic or necrotic cells that have lost membrane integrity from early apoptotic cells which still have intact membranes by dye exclusion. These assays can be readily adapted for use with any receptor and any phenotype.

The bioactive receptor, once identified, can be tested and used in practical applications in research and medicine. In particular, the compositions and methods described may be used identify effector molecules that alter, for example, gene expression, apoptosis, signal transduction, receptor activation, cell division, degranulation or any other detectable cellular phenotype.

EXAMPLES

The following examples are provided in order to demonstrate and further illustrate certain embodiments and aspects of the present invention and are not to be construed as limiting the scope thereof.

Example 1

Control of Composition of Multi-Component Gel Microdrops

Microdrops were made according to a protocol described by Gray et al (JIM 1995) by stiffing 16 ml of dimethylpolysiloxane (200 cSt, Sigma) in a 30 ml beaker with a 1 inch stir bar at 2000 rpm, at 37° C. While stiffing, a 600 µl suspension of particles in phosphate buffered saline (PBS) and 2% low gelling point agarose (Sigma Type IX) at 37° C., is added to create the emulsion. After stiffing for 2 minutes, the emulsion is chilled on ice while stiffing is continued for 2 minutes. This step solidifies the microdrops. The emulsion is then overlayed onto 20 ml of PBS in a 50 ml conical tube and centrifuged at 1000 rpm for 10 minutes. Under these conditions, the microdrops are pelleted at the bottom of the tube and rewashed twice in PBS. The microdrops are then resuspended in 1 ml of PBS and transferred to chamber slides or microwells for analysis.

Figure 2:
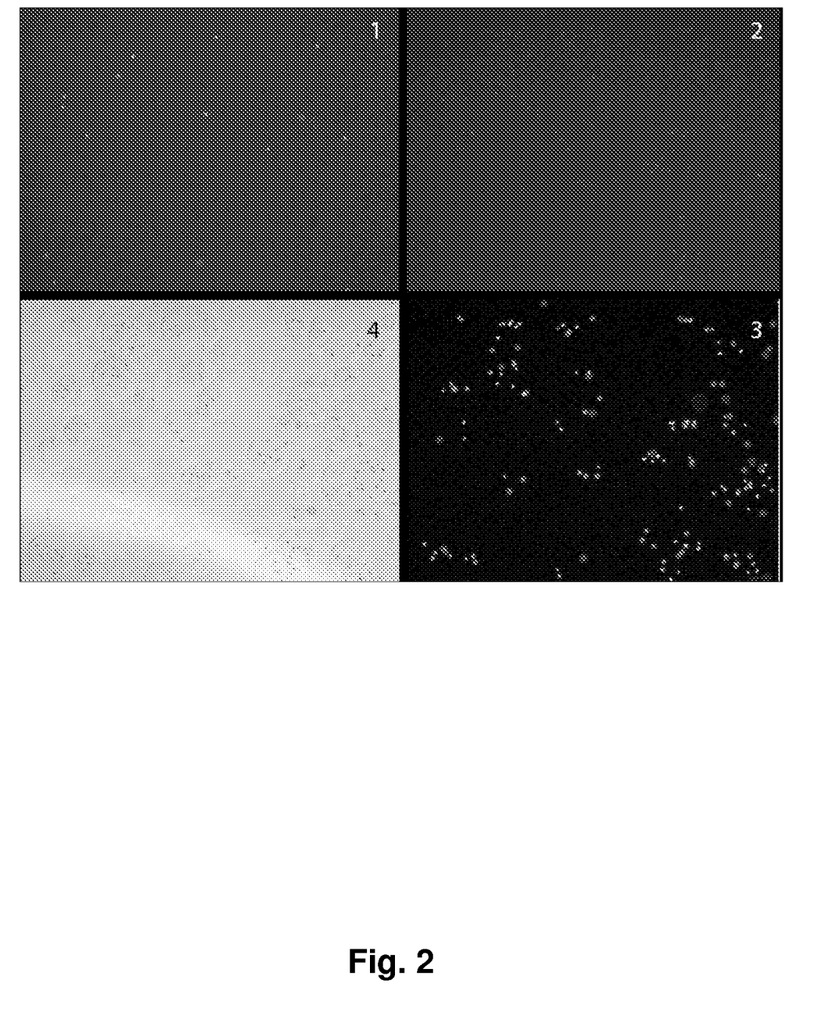
FIG. 2 shows four panels of images showing multiple particle types within agarose microdrops. Panel 1, blue channel; panel 2, green channel; panel 3, red channel; panel 4, brightfield.

Microdrops were prepared as described above with $5 \times 10^5$ red beads, $1 \times 10^5$ blue beads, and $2 \times 10^4$ green beads. All beads were 6 µm in size. Microdrops averaged ~150 µm in diameter, as determined by brightfield microscopy. All images shown in FIG. 2 were captured on a Leica DMI 6000 microscope. Z-stacks of each of the three fluorescence channels (red, green, and blue) plus brightfield were collected, flattened, and displayed as grayscale images. The images indicate the composition of microdrops with the expected bead ratios.

Example 2

Figure 3:
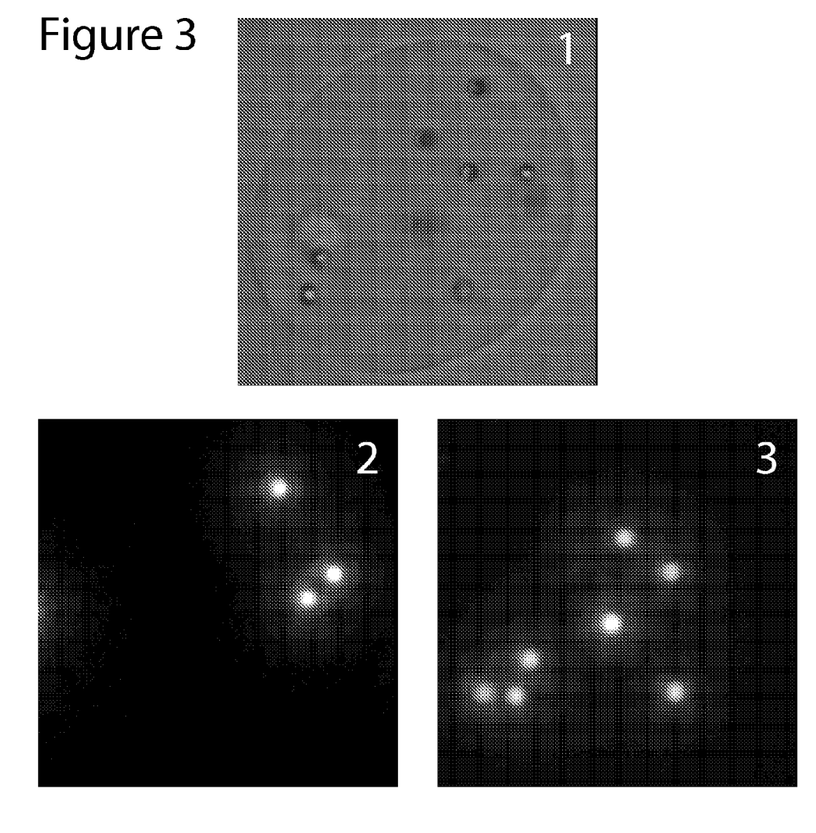
FIG. 3 shows three panels of images showing co-encapsulation of an effector cell with multiple reporters. Panel 1, brightfield; panel 2, red channel; panel 3, blue channel.

Microdrops Containing A Single Effector and Multiple Reporters Microdrops were prepared as described in Example 1 with $2 \times 10^4$ hybridoma cells, $1 \times 10^5$ red beads and $1 \times 10^5$ blue beads. All images shown in FIG. 3 are of the same field captured on a Leica DMI 6000 microscope. Z-stacks of red and green fluorescence channels were collected, flattened, and displayed as grayscale images. A brightfield z-stack was also collected, and a slice containing a single hybridoma cell is shown in FIG. 3.1. FIGS. 3.2 and 3.3, respectively, show three co-encapsulated beads on the red channel, representing Reporter 1, and seven co-encapsulated beads on the blue channel, representing Reporter 2.

Example 3

Demonstration of Antibody Specificity Assay within a Microdrop

A murine hybridoma, clone 141PF11 (ATCC), produces an antibody known to bind human kappa immunoglobulin light chain is co-encapsulated in a microdrop with two reporter bead types. Reporter 1 is prepared by coating 4.0 µm red polystyrene bead (Invitrogen, F8858) with purified human light chain (Sigma, K3388); Reporter 2 is a blue 4.0 µm polystyrene (Invitrogen F8854) bead that is coated with purified human lambda chain (Sigma, L0665). Microdrops are incubated at 37° C. in tissue culture media for 2 hours to allow antibody secretion from the hybridomas, and binding to the Reporters. Microdrops are washed and detecting antibody, goat anti-mouse FITC (Invitrogen, F-2761) is added to the microdrop suspension at 20 µg/ml for 1 hour. Microdrops are washed and placed into a microwell for imaging. The secreted antibody from hybridoma 141PF11 binds to Reporter 1 but not Reporter 2. This binding event is detected by goat anti-mouse IgG (FITC) polyclonal antibody. Microdrops containing this hybridoma are distinguished by the enhanced colocalization of the red and green signals, relative to the colocalization of the blue and green signals. Another hybridoma, clone HP6054 (ATCC), producing an antibody that binds to lambda but not kappa chains, and subjected to the same microdrop preparation and conditions as described above, shows colocalization of green signal with blue, but not red, beads. A third hybridoma, producing an antibody that binds to neither kappa nor lambda, shows no colocalization of green signal with either bead type.

Example 4

Generation of Isotype Specific Monoclonal Antibodies in a Novel Species

A chicken is immunized with human kappa chain. After 2 weeks it is boosted with antigen. Four days later, 10 million peripheral blood lymphocytes are isolated and are co-encapsulated in microdrops with reporter beads as described in Example 3. The microdrops are incubated with goat anti-chicken Ig (FITC), and screened at low magnification for any green signal significantly above background. These locations are recorded, and reimaged under higher magnification to resolve colocalization on the Reporter beads. Microdrops containing lymphocytes producing the desired anti-kappa profile (Red+Green colocalization only) are removed from the imaging plate with a manual pippetor and transferred to a fresh well. The gel matrix is dissolved with agarase and the liberated lymphocyte is cultured for 1-2 weeks in the presence of the appropriate chicken cytokines. From these cultured cells, cDNA is made and V genes are amplified by PCR and cloned into an expression vector. Plasmid DNA is transfected into CHO cells and recombinant antibodies are expressed and purified, and confirmed to react with human kappa chain.

Example 5

Generation of Monoclonal Antibodies from Splenic Germinal Center Cells

A chicken is immunized by intravenous injection of 1 mg of human kappa light chain. Six days later, the spleen is harvested and the germinal centers are isolated in a plastic petri dish containing 5 mls of ice-cold tissue culture medium. The splenic capsule is gently peeled away from the spleen mass using fine forceps and the pulp tissue is teased out into the surrounding medium. The arterial framework and associated germinal centers are then harvested to obtain B cells. The B cells are co-encapsulated in microdrops with reporter beds as described in Example 3 and grown for 10 days in the presence of cytokines such as CD40L that induce proliferation of chicken B cells. The microdrops are then incubated with goat anti-chicken Ig (FITC), and screened at low magnification for any green signal significantly above background. Microdrops containing lymphocytes producing the desired anti-kappa profile (Red+Green colocalization only) are removed from the imaging plate with a manual pipetor. cDNA is made from these selected effector cells, their V genes are amplified by PCR and then they are cloned into an expression vector. Plasmid DNA is transfected into CHO cells and recombinant antibodies are expressed and purified, and confirmed to react with human kappa chain.

Example 6

Identification of Agonistic Antibodies to Apoptotic Targets

A chicken is immunized with purified recombinant DR4 (Death Receptor 4, or TRAIL-R1), a protein known to be involved in the induction of an apoptotic pathway. In certain tumor-derived cell lines, DR4 can be engaged through its natural ligand, TRAIL, or through an antibody that mimics that ligand. Lymphocytes from a DR4 immunized chicken are co-encapsulated with Reporter 1, the human lymphoma cell line B9, and Reporter 2, normal human vascular endothelial cells (VEC). Reporter 1 and Reporter 2 are labeled with red and blue vital dyes, respectively. Microdrops are incubated in media containing SYTOX dye, a cell impermeant dye that stains DNA a bright fluorescent green; non-apoptotic cells do not absorb the dye but apoptotic cells do. Thus, an antibody having the desired effect of inducing apoptosis selectively in cancerous cells generates a green signal colocalized with Reporter 1, but not Reporter 2. Antibody genes from such microdrops are recovered as in Example 4.

Example 7

Identification of Bioactive Antibodies to Novel Targets

A rabbit is immunized with whole cells, or membrane fraction, of the lymphoma cell line B9. A microdrop based apoptosis assay is performed as in Example 6. Pro-apoptotic antibodies are recovered and targeted cell-surface molecules are identified.

Example 8

Agonistic Antibody to GPCR

Transfected 293 cells overexpressing the Dopamine receptor DRD1 are used to immunize chickens, and microdrops are generated to co-encapsulate immunized lymphocytes with reporter cells. Reporter 1 is a 293 cell expressing DRD1 and a GFP gene that is operably linked to a CRE responsive element. Reporter 2 is a 293 cell containing the same GFP gene but does not express DRD1. Reporter 1 and 2 are differentiated by red and blue vital dyes, respectively. When the DRD1 receptor is activated, signal transduction occurs through the alpha-s G-protein subunit, which ultimately activates CRE-linked genes, including the GFP transgene. Thus, when an antibody is produced that behaves as a specific agonist to DDR1, Reporter 1 develops green fluorescence, and Reporter 2 is dim on the green channel. In the case of a non-DDR1 antibody that can signal through a different mechanism, both Reporter 1 and 2 develop green fluorescence. A non-reactive antibody produces no green signal in either reporter.

Example 9

Bacterially Expressed Secretome Library

A library of human genes isolated from neuronal stem cells is cloned into an *E. coli* expression vector for the purpose of discovering novel factors capable of promoting the growth of neurons. Members of this library are seeded into small microdrops (e.g. 30 µm) at <1 bacterial cell per microdrop. Microdrops are placed into bacterial growth media and allowed to expand to form small colonies within each microdrop. These microdrops are now used as effector particles in a larger microdrop that contains non-dividing neuronal cells, loaded with red vital dye, as Reporter 1, and non-dividing fibroblasts, loaded with blue vital dye, as Reporter 2. Microdrops are cultured in mammalian cell culture media in the presence of FITC-dNTP. Microdrops are screened for colocalization of red and green, but not blue and green, signals. Such a profile is indicative of a potential neuronal specific growth factor being produced by the co-enapsulated bacterial colony. This colony is recovered and the expressed gene characterized.

What is claimed is:
1. A method for making gel microdrops comprising,
  a) combining:
    i. monomers that can be polymerized to produce a polymer;
    ii. antibody-producing cells;
    iii. first reporter particles that emit a first optically detectable signal; and
    iv. second reporter particles that emit a second optically detectable signal that is distinguishable from the first optically detectable signal;
  b) making droplets of the product of step a), wherein the droplets contain an antibody producing cell, at least one of said first reporter particles, and at least one of said second reporter particles; and
  c) polymerizing the monomers of the droplets produced by step b) to produce gel microdrops that comprise:
    a polymer matrix, an antibody-producing cell that secretes antibody into said polymer matrix,
at least one of said first reporter particles; and
at least one of said second reporter particles;
wherein, in said gel microdrops, said antibody-producing cell and said first and second reporter particles are encapsulated by said polymer matrix and wherein an alteration of said first or second optically detectable signal caused by selective binding interaction of said secreted antibody with one of said first or second reporter particles indicates that said secreted antibody is a selective binding agent.

2. The method of claim 1, wherein said first and second reporter particles are first and second cells.

3. The method of claim 2, wherein said first and second cells comprise fluorophores that produce said first and second optically detectable signals.

4. The method of claim 2, wherein said first and second cells comprise fluorescent proteins that produce said first and second optically detectable signals.

5. The method of claim 4, wherein said fluorescent protein of at least one of said first and second cells is encoded by an expression cassette comprising a polynucleotide encoding said fluorescent protein and an inducible promoter operably linked to said polynucleotide.

6. The method of claim 1, wherein said method comprises culturing the cells in said microdrops to allow for antibody production.

7. The method of claim 1, wherein said first and second reporter particles are beads.

8. The method of claim 1, wherein each of said gel microdrops comprises at least five first reporter particles and at least five second reporter particles.

9. The method of claim 1, wherein said polymer matrix is agarose.

* * * * *